US00PP31487P2

(12) United States Plant Patent
Ault

(10) Patent No.: US PP31,487 P2
(45) Date of Patent: Feb. 25, 2020

(54) ***PHLOX* PLANT NAMED 'PERFECTLY PUZZLING'**

(50) Latin Name: ***Phlox* hybrid**
Varietal Denomination: Perfectly Puzzling

(71) Applicant: James Robert Ault, Libertyville, IL (US)

(72) Inventor: James Robert Ault, Libertyville, IL (US)

(73) Assignee: CHICAGOLAND GROWS, INC, Glencoe, IL (US)

( * ) Notice: Subject to any disclaimer, the term of this patent is extended or adjusted under 35 U.S.C. 154(b) by 0 days.

(21) Appl. No.: 16/501,285

(22) Filed: Mar. 18, 2019

(51) Int. Cl.
*A01H 5/02* (2018.01)
*A01H 6/70* (2018.01)

(52) U.S. Cl.
USPC ..... Plt./320

(58) Field of Classification Search
USPC ..... Plt./320
CPC ..... A01H 5/02; A01H 6/70
See application file for complete search history.

*Primary Examiner* — Annette H Para
(74) *Attorney, Agent, or Firm* — Penny J. Aguirre

(57) ABSTRACT

A new cultivar of *Phlox* plant named, 'Perfectly Puzzling', that is characterized by its flowers that vary in color from near white to light to medium raspberry violet; the different color flowers can be evident on a plant at the same time, its petals that are non-overlapping, notched (bifid) and narrow resulting in a "starry" appearance that is unusual for a moss *Phlox*, its petals with medium to dark violet striae at the base, and its flowers that are smaller in size than most moss *Phlox*, however the flowers still cover the plants 100% at peak bloom.

2 Drawing Sheets

Botanical classification: *Phlox* hybrid.
Cultivar designation: 'Perfectly Puzzling'.

BACKGROUND OF THE INVENTION

The present invention relates to a new and distinct cultivar of *Phlox* plant of hybrid origin, botanically known as *Phlox* 'Perfectly Puzzling' and will be referred to hereafter by its cultivar name, 'Perfectly Puzzling'. The new cultivar represents a new herbaceous perennial grown for landscape use.

The new invention arose from an ongoing controlled breeding program by the Inventor in Glencoe, Ill. The objectives of the breeding program are to develop improved cultivars of interspecific hybrids of *Phlox* with novel ornamental traits such as unique flower colors, plant habits, flower fragrance and adaptability to garden conditions in the upper Midwest (U.S.D.A. Zone 5) and similar climates.

'Perfectly Puzzling' originated as a seedling that arose flow seed planted from open pollination of *Phlox subulata* 'Ellie B' (not patented) in May 2009. The seed parent was surrounded by numerous other cultivars and hybrids of *Phlox*. 'Perfectly Puzzling' was selected in April of 2012 as a single unique plant amongst the resulting seedlings.

Asexual propagation of the new cultivar was first accomplished by shoot tip cuttings by the Inventor in June of 2012 in Glencoe, Ill. Asexual propagation by shoot tip cuttings has determined that the characteristics of this cultivar are stable and reproduced true to type in successive generations.

SUMMARY OF THE INVENTION

The following traits have been repeatedly observed and represent the characteristics of the new cultivar. These attributes in combination distinguish 'Perfectly Puzzling' as a unique cultivar of *Phlox*.

1. 'Perfectly Puzzling' exhibits flowers that vary in color from near white to light to medium raspberry violet; the different color flowers can be evident on a plant at the same time.
2. 'Perfectly Puzzling' exhibits petals that are non-overlapping, notched (bifid) and narrow resulting in a "starry" appearance that is unusual for a moss *Phlox*.
3. 'Perfectly Puzzling' exhibits petals with light to dark violet striae at the base.
4. 'Perfectly Puzzling' exhibits flowers that are smaller in size than most moss *Phlox*, however the flowers still cover the plants 100% at peak bloom.

The female parent of 'Perfectly Puzzling', 'Ellie B', differs from 'Perfectly Puzzling' in having flowers that are all white in color and smaller in width, and petals that have no striae, and that are broader and overlap at their bases. 'Perfectly Puzzling' can also be compared to the *Phlox* cultivars 'Snowflake' (not patented) and 'Snow Queen' (not patented). 'Snowflake' and 'Snow Queen' are both similar to 'Perfectly Puzzling' in flower size and in having distinctly notched (bifid) petal tips. 'Snowflake' differs from 'Perfectly Puzzling' in having flower petals that are all white in color with no striae and visible anthers at the top of the corolla throat with conspicuous orange yellow pollen, which are buried in the corolla throat on 'Perfectly Puzzling' flowers. 'Snow Queen' differs from 'Perfectly Puzzling' in having flower petals that are all white in color with no striae and that are broader and overlap at their bases.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosure and/or sales prior to the filing date but less than one year prior to the effective filing date.

BRIEF DESCRIPTION OF THE DRAWINGS

The accompanying colored photographs illustrate the overall appearance and distinct characteristics of the new *Phlox*. The photographs were taken of 'Perfectly Puzzling' as grown in a trial garden in Glencoe, Ill.

The photograph in FIG. 1 provides a view of the plant habit of a block of 5-year-old plants of 'Perfectly Puzzling'.

Figure 1:
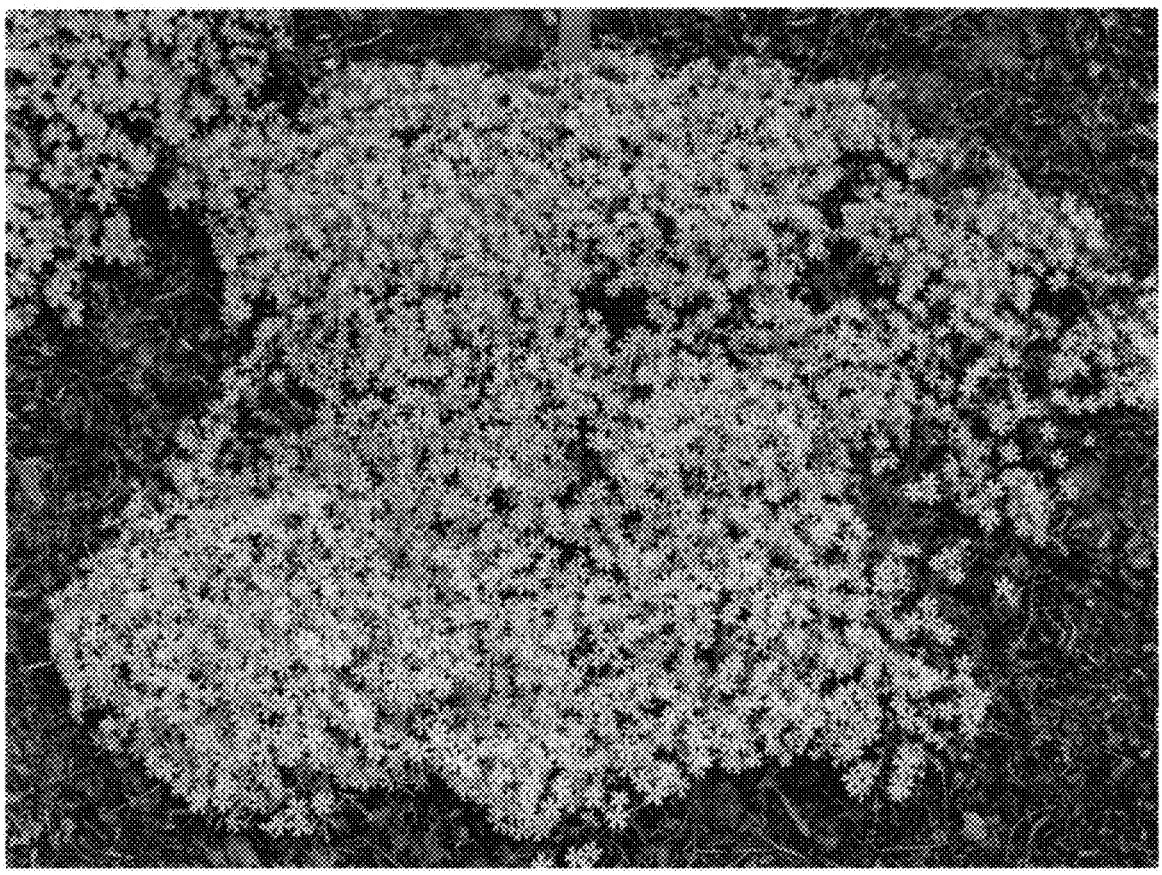
Figure 2:
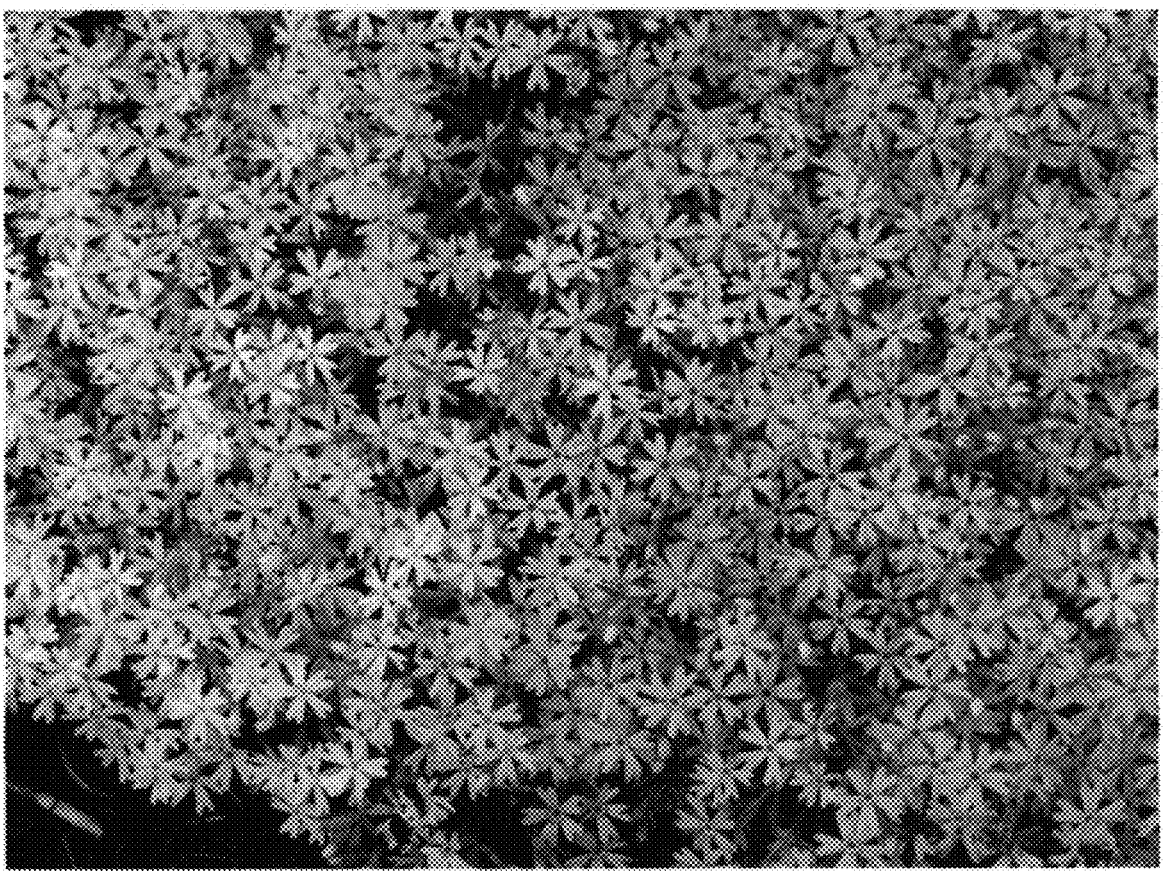

The photograph in FIG. 2 provides a view of the inflorescences of 4-year-old plants of 'Perfectly Puzzling'.

The colors in the photographs are as close as possible with the photographic and printing technology utilized and the color values cited in the Detailed Botanical Description accurately describe the colors of the new *Phlox*.

DETAILED BOTANICAL DESCRIPTION OF THE PLANT

The following is a detailed description of nine month-old plants of the new cultivar as grown in 4-inch containers in Glencoe, Ill. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period.*—Four to five weeks beginning in mid to late April until mid to late May in northern Illinois.

*Plant habit.*—Vigorous, broad spreading plant habit that readily layers into a groundcover.

*Height and spread.*—In-ground trial plants 3 years in age; 40 cm in width and 12 cm in height at peak bloom, in-ground trial plants 4 years in age; 47 cm in width and 11 cm in height at peak bloom.

*Hardiness.*—At least hardy in U.S.D.A. Zones 4 to 7.

*Diseases and pests.*—Good resistance to powdery mildew (caused by *Erysiphe cichoracearum*) has been observed.

*Root description.*—Fibrous, 161D in color.

*Growth rate.*—Good vigor.

*Propagation.*—Shoot tip cuttings.

*Root development.*—Shoot tip cuttings will root under mist in 4 to 5 weeks in late spring to early summer, rooted cutting will fully root in a 2.5 inch pot in about 3 months and when tranplanted in fall and overwintered in a 4-inch pot, they will bloom the following spring.

Stem description:

*Stem size.*—An average of 6 cm in length and 1.5 mm in width.

*Stem shape.*—Round-oval.

*Stem strength.*—moderately strong.

*Stem color.*—N144D.

*Stem surface.*—Smooth, slightly glossy, and densely covered with wooly hairs about 0.5 mm in length.

*Stem aspect.*—Held upright to trailing.

*Internode length.*—An average of 9 mm.

*Branching habit.*—Well branched an average of 20 stems from base with an average of 4 flowering branches per basal stem.

Foliage description:

*Leaf shape.*—Lanceolate.

*Leaf division.*—Simple.

*Leaf base.*—Truncate to clasping.

*Leaf apex.*—Narrowly acute.

*Leaf venation.*—Pinnate, inconspicuous, matches leaf color on upper and lower surfaces.

*Leaf margins.*—Entire and sparsely covered in fine hairs about 0.7 mm in length.

*Leaf attachment.*—Sessile.

*Leaf arrangement.*—Opposite.

*Leaf surface texture.*—Smooth and shiny on upper and lower surfaces.

*Leaf color.*—Upper surface; 138A, lower surface; 138A to 138B.

*Leaf size.*—Up to 2 cm in length and 3 mm in width.

*Leaf quantity.*—An average of 14 leaves per stem.

*Leaf fragrance.*—None.

Flower description:

*Inflorescence type.*—Panicle on terminus of main stems and lateral branches.

*Lastingness of inflorescence.*—About 3 to 4 weeks from the opening of the first flower to senescence of last flower, individual flower lasts about 5 days.

*Inflorescence size.*—An average of 3 cm in height and 3.5 cm in diameter.

*Flower fragrance.*—Light floral scent.

*Flower number.*—An average of 3 per inflorescence.

*Flower aspect.*—Upright to outward.

*Flower bud.*—Spatulate in shape, acute apex, an average of 1.4 cm in length and 2.5 mm in width, color; petal portion N155B or N155B and calyx portion 138C with stripes of 137D, surface of petal portion glabrous and sepal portion pubescent.

*Flower form.*—Salverform.

*Flower size.*—An average of 1.5 cm in height and 1.45 cm in diameter.

*Corolla tube.*—An average of 1.2 cm in length and 1.8 mm in width, color; N155B with some suffused with 76B on both surfaces, surface glabrous, satiny and ridged.

*Corolla lobes.*—5, obcordate in shape, held nearly horizontally when fully open, non-overlapping, an average of 8 mm in length and 4.5 mm in width, apex bifid with a cleft 2 mm in depth and width, apex of lobes rounded, base broadly cuneate and fused to tube, entire margins, color: 3 different colors observed, one color (lightest); upper surface when opening; 76D with a distinct pair of striae 77A near base, lower surface when opening; 76C to 76D, upper surface when fully open; a blend of 76B and 76C and a pair of striae 76A near base, lower surface when fully open; 76C, second color; upper surface when opening; a blend of 76C and 76D with a distinct pair of striae 77A near base, lower surface when opening; a blend of 76B to 76C, upper surface when fully open; a blend of 76A and a pair of striae 76B near base, lower surface when fully open; 76B, third color; upper surface when opening; 76A a distinct pair of striae N82A near base, lower surface when opening; 76B and slightly suffused with 76A, upper surface when fully open; N82B to N82C with a pair of striae N82A near base, lower surface when fully open; N82C, glabrous and slightly satiny surface texture on upper and lower surfaces.

*Calyx.*—Campanulate in form, comprised of fused sepals with linear shaped sepal tips free, an average of 6 cm in length and 2.5 mm in width.

*Sepals.*—5, primarily fused with free tips, linear in shape, entire margins, fused base (about 50%), aristulate apex, an average of 6 mm in length and 1 mm in width, inner surface texture; glabrous and shiny, outer surface texture; densely covered with wooly hairs about 1 mm in length, color on inner and outer surface; 138A and 138C near the base.

*Peduncles.*—Rounded in shape, an average of 1.4 cm in length and 1.5 mm in width, held upright to outward, surface; color; 138B, smooth and pubescent with wooly hairs about 0.5 mm in length, 2 peduncle leaves; up to 9 mm in length and 2 mm in width, all other characteristics the same as stem leaves.

*Pedicels.*—Rounded in shape, an average of 9 mm in length and 1 mm in width, held upright to outward, surface; color 138C, smooth and pubescent with wooly hairs about 0.5 mm in length, held upright to an average angle of 45° to peduncle.

Reproductive organs:

*Gynoecium.*—1 pistil; stigma; tri-lobed, each lobe is about 1.5 mm in length and 12D in color, style is about 9 mm in length and 0.3 mm in width, and 138D in color, ovary; superior, oval in shape, about 1 mm in length and 0.7 mm in width, and 138B in color.

*Androcoecium.*—5 stamens; anthers; dorsifixed, oblong in shape, an average of 1 mm in length, and 165C in color, filaments; adnate to petals, an average of 6 mm in length and N155A in color, pollen is moderate in quantity and 14C in color.

*Seeds.*—None observed to date.

It is claimed:

1. A new and distinct cultivar of *Phlox* plant named 'Perfectly Puzzling' as herein illustrated and described.

* * * * *